(12) United States Patent
Ballesteros et al.

(10) Patent No.: US 12,205,048 B2
(45) Date of Patent: *Jan. 21, 2025

(54) DATA PROCESSING SYSTEM TO DETECT NEURODEVELOPMENTAL-SPECIFIC LEARNING DISORDERS

(71) Applicant: Carnegie Mellon University, Pittsburgh, PA (US)

(72) Inventors: Miguel Ballesteros, Pittsburgh, PA (US); Maria Luz Rello-Sanchez, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/743,156

(22) Filed: May 12, 2022

(65) Prior Publication Data

US 2023/0105867 A1 Apr. 6, 2023

Related U.S. Application Data

(63) Continuation of application No. 15/493,060, filed on Apr. 20, 2017, now Pat. No. 11,334,803.

(Continued)

(51) Int. Cl.
*G06N 5/04* (2023.01)
*G06N 3/044* (2023.01)
(Continued)

(52) U.S. Cl.
CPC .............. *G06N 5/04* (2013.01); *G06N 3/044* (2023.01); *G06N 20/00* (2019.01); *G06N 20/10* (2019.01); *G16H 50/20* (2018.01)

(58) Field of Classification Search
CPC .......... G06N 5/04; G06N 20/00; G06N 20/10; G06N 3/0445; G16H 50/20
See application file for complete search history.

(56) References Cited

U.S. PATENT DOCUMENTS 9,672,618 B1 * 6/2017 Hassanain ............ A61B 3/0033
10,114,860 B1 * 10/2018 Wittenstein ............ G06F 16/20
(Continued)

OTHER PUBLICATIONS

Adler-Grinberg et al., "Eye movements, scanpaths, and dyslexia," American Journal of Optometry and Physiological Optics, 1978, 55(8):557-570.

(Continued)

*Primary Examiner* — Malina D. Blaise
(74) *Attorney, Agent, or Firm* — Fish & Richardson P.C.

(57) ABSTRACT

This document describes a data processing system for processing a feature vector that comprises features (one or more) that are indicative of dyslexic behavior that are indicative of dyslexic behavior. The data processing system includes a feature classification engine that generates classification metrics for a feature vector. Machine learning logic is used to determine a classification metric for each feature. Features that have a classification metric below a pre-determined threshold are removed. The data processing system includes a prediction engine that generates a prediction value indicative of a predicted likelihood of dyslexia. The prediction engine assigns, to each remaining feature, based on the classification metric of the respective remaining feature, a prediction weight and determines the prediction value based on the prediction weights.

20 Claims, 6 Drawing Sheets

Related U.S. Application Data

(60) Provisional application No. 62/497,105, filed on Nov. 9, 2016, provisional application No. 62/391,144, filed on Apr. 20, 2016.

(51) Int. Cl.
  G06N 20/00 (2019.01)
  G06N 20/10 (2019.01)
  G16H 50/20 (2018.01)

(56) References Cited

U.S. PATENT DOCUMENTS

| | | | |
|---|---|---|---|
| 10,423,709 B1* | 9/2019 | Bradley | G06F 40/16 |
| 10,885,478 B2* | 1/2021 | Roberts | G06F 16/24578 |
| 11,334,803 B2 | 5/2022 | Luz Rello-Sanchez et al. | |
| 2004/0049124 A1* | 3/2004 | Kullok | A61B 5/163 |
| | | | 600/558 |
| 2005/0084880 A1* | 4/2005 | Duman | C12Q 1/6883 |
| | | | 435/6.16 |
| 2006/0166174 A1* | 7/2006 | Rowe | G09B 5/06 |
| | | | 434/236 |
| 2008/0208072 A1* | 8/2008 | Fadem | A61B 5/726 |
| | | | 600/544 |
| 2009/0327883 A1* | 12/2009 | Robertson | G06F 16/44 |
| | | | 707/999.102 |
| 2010/0184009 A1* | 7/2010 | Rajkowski | G09B 5/02 |
| | | | 434/159 |
| 2012/0066238 A1* | 3/2012 | Fadem | A61B 5/291 |
| | | | 707/E17.014 |
| 2014/0364761 A1* | 12/2014 | Benson | A61B 5/163 |
| | | | 600/558 |
| 2015/0118661 A1* | 4/2015 | Haruta | G06F 19/3481 |
| | | | 434/169 |
| 2017/0261584 A1* | 9/2017 | James | G01R 33/4833 |
| 2017/0287356 A1* | 10/2017 | Stephen | G09B 7/06 |
| 2017/0347874 A1* | 12/2017 | Novik | G06F 3/016 |
| 2018/0308473 A1* | 10/2018 | Scholar | G10L 15/18 |
| 2020/0051697 A1* | 2/2020 | Krishnamurti | G06N 20/00 |

OTHER PUBLICATIONS

British Dyslexia Association. 2012. Dyslexia Style Guide. (Jan. 2012). littp ://www.bdadyslexia.org.uk/, 1-4.

Bruck, "Persistence of dyslexics phonological awareness defecits," Developmental psychology 1992, 28(5):874-886.

Bruck, "The word recognition and spelling of dyslexic children." Reading Research Quarterly, Jan. 1988, 51-69.

Carreiras et al., "Effect of word and syllable frequency on activation during lexical decision and reading aloud," Human brain mapping, 2006, 27(12):963-972.

Chang et al., "LIBSVM: A library for support vector machines," ACM Transactions on Intelligent Systems and Technology, 2011, 2:27:1-27:27, Software available at http://www.csie.ntu.edu.twl-cjiinilibsyrn.

Cuetos et al., "Modelos de lectura y dislexias," (Reading models and dyslexias). Infancia y Aprendizaje (Infancy and Learning), 1988, 44:3-19.

Cunningham Gabe Zichermann, "Gamification by Design: Implementing Game Mechanics in Web and Mobile Apps," O'Reilly, 2011, 1-210.

Eden et al., "Differences in eye movements and reading problems in dyslexic and normal children," Vision Research, May 1994, 34(10):1345-1358.

Elterman et al., "Eye movement patterns in dyslexic children," Journal of Learning Disabilities, 1980, 13(1):16-21.

Everatt et al., "Individual differences in reading and eye movement control", Eye guidance in reading and scene perception, 1998, 223-242.

Facoetti et al., "Visual-spatial attention in developmental dyslexia," Cortex, 2000, 36(1):109-123.

Gaggi et al., "A serious game for predicting the risk of developmental dyslexia in pre-readers children.," In Proc. ICCCN'12.IEEE, 2012, 1-5.

Granka et al., "Eye-tracking analysis of user behavior in www search," In Proceedings of the 27th annual international ACM SIGIR conference on Research and development in information retrieval, 2004, 478-479.

Grund et al., "Diagnostischer Rechtschreibtest fur 5. Klassen: DRT 5"; Manual. Deutsche Schultests. Beltz Test, Gottingen, 2., aktual. aufl. in neuer rechtschreibung edition, 2004, 1-8.

Hyona et al., "Eye fixation patterns among dyslexic and normal readers: Effects of word length and word frequency," Journal of Experimental Psychology: Learning, Memory, and Cognition, 1995, 21(6):1430-1440.

Inhoff et al., "Parafoveal word processing during eye fixations in reading: Effects of word frequency," Perception & Psychophysics, 1986, 40(6):431-439.

Judd et al. "Learning to predict where humans look," In Computer Vision, 2009 IEEE 12th international conference, 2009, 2106-2113.

Just et al., "A theory of reading: From eye fixations to comprehension," Psychological review, 1980, 87(4):329-354.

Lyytinen et al., "Early identification of dyslexia and the use of computer game-based practice to support reading acquisition," Nordic Psychology, 2007, 59(2):109-126.

Lyytinen et al., "In search of a science-based application: A learning tool for reading acquisition," Scandinavian journal of psychology, 2009, 50(6):668-675.

Mohtaram et al., "Mobile Dyslexia Screening Test: A New Approach through Multiple Deficit Model Mobile Game to Screen Developmental Dyslexia Children," In Malaysia University Conference Engineering Technology, 2014, 1-9.

Nation et al., "Investigating individual differences in childrens real-time sentence comprehension using language-mediated eye movements," Journal of Experimental Child Psychology, 2003, 86(4):314-329.

Olson et al., "Individual and developmental differences in reading disability," Reading research: Advances in theory and practice, 1985, 4:1-64.

Paulesu et al., "Dyslexia: Cultural diversity and biological unity," Science, Nov. 2001, 291(5511):2165-2167.

Pirozzolo et al., "2—The Neural Control of Eye Movements in Acquired and Developmental Reading Disorders," Studies in Neurolinguistics, 1979, 4:97-123.

Raney et al., "Word frequency effects and eye movements during two readings of a text," Canadian Journal of Experimental Psychology, 1995, 49(2):151-173.

Rayner et al., "Eye movement control in reading and visual search: Effects of word frequency," Psychonomic Bulletin & Review, 1996, 3(2):245-248.

Rayner et al., "Lexical complexity and fixation times in reading: Effects of word frequency, verb complexity, and lexical ambiguity," Memory & Cognition, 1986, 14(3):191-201.

Rayner, "Eye movements and the perceptual span in older and younger readers," Psychology and Aging, 2009, vol. 24(3):755-760.

Rayner, "Eye movements in reading and information processing: 20 years of research," Psychological Bulletin, 1998, 124:372-422.

Rayner, "The role of eye movements in learning to read and reading disability," Remedial and Special Education, Nov. 1985, 6(6):53-60.

Rello et al., "DysList: An Annotated Resource of Dyslexic Errors," In Proc. LREC, 2014, 1289-1296.

Rello et al., "Good fonts for dyslexia," In Proc. ASSETS'13, Bellevue, Washington, USA, 2013, 1-8.

Rello, "DysWebxia. A Text Accessibility Model for People with Dyslexia," PhD thesis, Universitat Pompeu Fabra, 2014, 1-504.

Serrano et al. "Dyslexia speed problems in a transparent orthography," Annals of Dyslexia, 2008, 58(1):81-95.

Sterling et al., "Adult dyslexic writing." Dyslexia 4.1, Mar. 1998, 1-15.

Temple et al., "Neural deficits in children with dyslexia ameliorated by behavioral remediation: evidence from functional MM," Proceedings of the National Academy of Sciences, 2003, 100(5):2860-2865.

(56) References Cited

OTHER PUBLICATIONS

Tinker, "Recent studies of eye movements in reading," Psychological Bulletin, 1958, 55(4):215-231.
Tinker, "The study of eye movements in reading," Psychological Bulletin, 1946, 43(2):93-120.
Tops et al., "Identifying students with dyslexia in higher education," Annals of dyslexia, 2012, 62(3):1-36.
Toro et al., "TALE: Test de An'alisis de Lectoescritura (TALE: Literacy Analysis Test)", Visor, Madrid, 1984, 1-191.
Tressoldi et al., "The development of reading speed in Italians with dyslexia a longitudinal study," Journal of learning disabilities, 2001, 34(5):414-417.
Van den Audenaeren et al., "DYSL-X: Design of a tablet game for early risk detection of dyslexia in preschoolers," In Games for Health, 2013, 257-266.
Vellutino et al., Specific reading disability (dyslexia): What have we learned in the past four decades? Journal of Child Psychology and Psychiatry, 2004, 45(1):2-40.
Ziegler et al., "Reading acquisition, developmental dyslexia, and skilled reading across languages: a psycholinguistic grain size theory, " Psychological bulletin, 2005, 131(1): 3-29.

\* cited by examiner

300

| Exercise Type | Cognitive Skill | Example | Exercise Type | Cognitive Skill | Example |
|---|---|---|---|---|---|
| Stage 1 Letter Recognition by Name | Orthographic Processing | u i e / i e u / e o i | Stage 2 Letter Recognition by Sound | Phonological Awareness | c g c d / a e g g / d c b d / e d b c |
| Stage 3 Syllable Recognition by Sound | Phonological Awareness | qu nu ba an / ad qu na ba / ab eb de ap / an an ne eb | Stage 4 Word Recognition by Sound | Word Recognition | pala mala sala / gala sala dala / pala mala dala |
| Stage 5 Non-word Recognition by Sound | Phonological Memory | pedana madaga pedana / depana banaga banaga / danaga panada madapa | Stage 6 Letter Differentiation | Visual Attention | n n n u / n n n n / n n n n / n n n n |
| Stage 7 Insertion of Letter | Phonological Awareness | lu_es / s c m i u | Stage 8 Substitution of Letter | Error Correction, Phonological Awareness | h a(z)e r / b t d l |
| Stage 9 Letter Ordering | Phonemic Segmentation & Phonological Awareness | s e i t e | Stage 10 Syllable Ordering | Syllabic Segmentation and Phonological Awareness | be da bi |
| Stage 11 Sentence Segmentation | Word Recognition | L a p a l o n a | Stage 12 Deletion of Letter | Phonological Awareness | b e b d e r |
| Stage 13 Error Detection | Syntactic Awareness | Esta la final de la sala. | | | |
| Stage 14 Error Detection | Semantic Awareness | Voy a la pasterleria a comparar un pastel. | | | |
| Stage 15 Letter Sequence Memorization | Visual Memory and Working Memory | | | | |
| Stage 16 Word Dictation | Word Writing | pgdj | q w e r t y u i o p / a s d f g h j k l / z x c v b n m | | |
| Stage 17 Non-word Dictation | Non-word Writing and Phonological Memory | | | | |

FIG. 3

| Only | Accuracy | | Without | Accuracy |
|---|---|---|---|---|
| 1 | 72.17% | | 1 | 75.94% |
| 2 | 70.75% | | 2 | 74.06% |
| 3 | 65.09% | | 3 | 76.42% |
| 4 | 67.92% | | 4 | 76.42% |
| 5 | 69.34% | | 5 | 78.30% |
| 6 | 61.79% | | 6 | 79.25% |
| 7 | 71.70% | | 7 | 76.42% |
| 8 | 74.06% | | 8 | 76.42% |
| 9 | 74.53% | | 9 | 76.89% |
| 10 | 72.17% | | 10 | 79.72% |
| 11 | 72.17% | | 11 | 77.36% |
| 12 | 64.62% | | 12 | 77.83% |
| 13 | 68.40% | | 13 | 78.77% |
| 14 | 63.68% | | 14 | 81.13% |
| 15 | 73.11% | | 15 | 81.60% |
| 16 | 75.94% | | 16 | 79.72% |
| 17 | 73.11% | | 17 | 83.49% |

| | Score |
|---|---|
| Accuracy | 83% |
| Precision – Class Dyslexia | 36.0% |
| Recall – Class Dyslexia | 90.0% |
| Precision – Class Not-Dyslexia | 98.7% |
| Recall – Class Not-Dyslexia | 82.2% |

FIG. 5

DATA PROCESSING SYSTEM TO DETECT NEURODEVELOPMENTAL-SPECIFIC LEARNING DISORDERS

CLAIM OF PRIORITY

This application claims priority under 35 U.S.C. § 120 to U.S. patent application Ser. No. 15/493,060, filed on Apr. 20, 2017, which claims priority under 35 USC § 119(e) to U.S. Patent Application Ser. No. 62/391,144, filed on Apr. 20, 2016, and U.S. Patent Application Ser. No. 62/497,105, filed on Nov. 9, 2016, the entire contents of which are hereby incorporated by reference.

GOVERNMENT RIGHTS

This invention was made with government support under H133A130057 awarded by the National Institute on Disability and Rehabilitation Research. The government has certain rights in this invention.

BACKGROUND

Dyslexia, an example of a neurodevelopmental-specific learning disorder, is characterized by difficulties with accurate and/or fluent word recognition and by poor spelling. Dyslexia is difficult to detect. Even in the UK, a country that effectively treats dyslexia as compared with other countries, only 5% of the individuals with dyslexia are diagnosed and given appropriate help; it is estimated that over 85% of adult illiterates have dyslexia. Even if research agrees in the neurological universality of dyslexia, its manifestations are different across languages, depending on the grade of regularity of the language orthographies. For instance, English has an opaque—or deep—orthography (the relationships between letters and sounds are inconsistent) and Spanish has a transparent—or shallow—orthography with more consistent mappings between letters and sounds. While dyslexia manifestation in languages with opaque orthographies are related to reading and writing performance, the manifestations of dyslexia in languages with shallow orthographies are not that evident, with reading speed and fluency the main predictors [20]. While in an English speaking country a child that reads slower but accurate might not been diagnosed with dyslexia; in a Spanish speaking country he or she could be diagnosed as dyslexic. In fact, dyslexia has been called a hidden disability due to the difficulty of its diagnosis in languages with shallow orthographies.

More than 10% of the population has dyslexia. For instance, the U.S. Congress reported that from 10 to 17.5% of the population has dyslexia. Dyslexia has a neurological origin, and results in difficulty with reading and writing. If people know they have dyslexia, they can train with effort over time to overcome its negative effects. When people with dyslexia are not diagnosed and provided with appropriate support, they often fail in school. For instance, the Spanish Ministry of Education states that over 40% of the school dropout rate is due to dyslexia. School failure is a primary way that people first learn that they might have dyslexia, which often comes too late for effective intervention. The primary reasons that students are not properly diagnosed is that current procedures for diagnosis are expensive and require professional oversight. Furthermore, practitioners and teachers tell us that children often dislike these tests, which is yet another reason why children and teachers are unlikely to complete them. As a result, even though it is known how to detect and diagnose dyslexia, with current approaches most children will be diagnosed late. The goal is for a user to know as early as possible if he or she might have dyslexia. The data processing system described herein facilitates discovery and reduces costs of discovery of dyslexia in patients.

In this order, Lyytinen et al. [15] created the computer game Literate, later called GraphoGame [14], 1 to identify children at risk of having dyslexia before school age in Finland. Its exercises are aimed towards the connection of graphemes (letters) and phonemes (sounds). They conducted two user studies with 12 and 41 children between 6 and 7 years old with promising results. The authors provide statistical differences between populations but they do not run any machine learning prediction model. In comparison the data processing system can be configured for people from all ages starting from 7 years old and cover a wider spectrum of cognitive skills including different levels of language and attentional abilities.

Prior game-centric approaches to predict dyslexia in prereaders did not report any prediction results. First, Gaggi et al. [12] tested a game with 24 pre-school students in Italy, which aimed at eye-hand coordination, visual spatial attention, rapid speech-sound identification and discrimination as well as visual to-speech sound. Second, Van den Audenaeren et al. [25] performed a user study with 20 pre-school students in Flanders and developed the game DYSL-X for early risk detection of dyslexia, which includes letter and endphoneme recognition as well as psycho-acoustical tests. Similar to previous approaches, another mobile game is developed at its initial phase in Malaysia by Mohtaram et al. [17].

Worldwide, around 15-20% of the population has a language based learning disability. Likely, 70-80% of these have dyslexia. Dyslexia is defined as a specific learning disability with neurological origin. It is characterized by difficulties with accurate and/or fluent word recognition and by poor spelling and decoding abilities. These difficulties typically result from a deficit in the phonological component of language that is often unexpected in relation to other cognitive abilities. Secondary consequences may include problems in reading comprehension and reduced reading experience that can impede growth of vocabulary and background knowledge. The most frequent way to detect a child with dyslexia is by his or her low-performance at school. While the average of school failure in the European Union is around 15%, Spain has around 25-30% of school failure, 31% in 2010.

However, despite its universal neuro-cognitive basis, dyslexia manifestations are language dependent [34]. Dyslexia variability is due to the different language orthographies depending on their grade of consistency and regularity. English has an opaque—or deep— orthography in which the relationships between letters and sounds are inconsistent and many exceptions are permitted. English presents to the beginning reader a significantly greater challenge compared to other languages, such as Spanish. Spanish has a more regular alphabetic system containing consistent mappings between letters and sounds, that is, a transparent—or shallow— orthography. For instance, Italian readers with dyslexia—shallow orthography— performed better on reading tasks than English and French readers with dyslexia—deep orthographies [45].

Although dyslexia is a frequent condition, only a small percentage of people with dyslexia are diagnosed. For instance, in the UK only 5% of individuals with dyslexia are diagnosed and given appropriate help, it is estimated that over 85% of adult illiterates have dyslexia. Dyslexia diagnoses depend on the language. In languages with deep orthographies the indicators used to detect individuals with dyslexia are their accuracy at word reading, non-word reading, word spelling, and phonological awareness [58, 61]. In languages with transparent orthographies slower reading speed is a stronger indicator [55, 60], hence its detection is more challenging. In fact, dyslexia has been called a hidden disability due to the difficulty of its diagnosis in languages with shallow orthographies [61].

Dyslexia detection is crucial. When diagnosed, dyslexia can be treated avoiding its consequences such as high rates of academic failure. At the same time diagnosing dyslexia is not a trivial task; it is expensive and it normally requires an expert. Also, dyslexia manifestations vary depending on the language.

Traditional paper based diagnosis of dyslexia such as TALE [59] for Spanish or Diagnostischer Rechtschreibtest [36] for German, analyze both reading and writing skills. Diagnoses of dyslexia are confirmed when the reading and the spelling performance of the child is significantly under the level expected due to her or his age and general intelligence.

Neuroimaging with children with dyslexia has revealed relationships between brain responses at infancy and later reading performance. Molfese reported that there are brain responses (event-related brain potentials) to speech sounds within 36 hours of birth that can be used to discriminate children who would become readers with dyslexia with 8 years old. The accuracy of this prediction is 81%.

Regarding eye tracking, previous eye tracking studies with people with dyslexia from psychology research have concluded that the eye movements of people with dyslexia are not the cause but the reflection of the difficulties they have while reading [37, 46, 49]. Although there are a number of studies that present how eye tracking measures show individual differences [33, 43, 49], most of the studies agree in finding significant differences among readers with and without dyslexia.

Rayner [50] presents a review of the studies from the mid 70's to the 90's that have used eye movements to investigate cognitive processes. He argues that eye movement measures can be used to infer moment-to-moment cognitive processes in reading. For instance, shorter fixations are associated with better readability while longer fixations can indicate that processing loads are greater. As a matter of fact, non-impaired readers present longer fixations at low-frequency words than at high-frequency words [38, 40, 47, 51, 52].

The eye movements of readers with dyslexia are different from regular readers. People with dyslexia as well as beginner readers, make longer fixations, more fixations, shorter saccades (rapid movement of the eye between fixation points) and more regressions than readers without dyslexia [28, 31, 32].

The impact of text presentation and text content on the readability and comprehension of people with dyslexia was previously explored [53]. In all the experiments, significant differences between participants with and without dyslexia regarding eye tracking measures were found. Indeed, previous work regarding eye movements and dyslexia have found patterns, classifications, individual differences, and significant differences between populations. However, none of them have applied machine learning to classify people with and without dyslexia, that is, to detect readers with dyslexia as the data processing system described herein.

SUMMARY

This patent presents three data processing systems. Method 1: Method 1 is based on human computer interaction measures extracted from linguistic and attentional games and how they can be used to detect dyslexia. Method 2: Method 2 is based on eye-tracking data and how they can be used to detect dyslexia. Method 3: Method 3 is based on mouse-tracking data and how they can be used to detect dyslexia.

(Method 1) The data processing system described herein differs from prior approaches in its content design and prediction model. First, the content of the data processing system includes exercises based on (i) the empirical linguistic analyses of the errors that people with dyslexia make, (ii) principles of language acquisition, and (iii) specific linguistic skills related to dyslexia. Second, this is the first game to use human-computer interaction measures to train a machine learning model to predict dyslexia. Further, the data processing system includes the first game that aims at screening dyslexia in Spanish applying machine learning to measures extracted from linguistic and attentional exercises designed on the basis of generated content by people with dyslexia, and can be applied to other languages.

(Method 1) Described herein is a method to detect individuals with or at risk of neurological learning disabilities, such as Dyslexia, using human computer interaction including eye-tracking, mouse tracking and different types of reading and writing performance. One aspect of the data processing system presents a statistical model to predict readers with and without dyslexia using eye tracking measures, and this model can be adapted for other human computer interactions. An important consideration of the present method combines the use of machine learning and the human computer interaction to achieve enhanced detection results.

(Method 1) This document describes a scalable early detection system and method via machine learning models that predict reading and writing difficulties by recording how people interact with a linguistic web-based game, representing a wide variety of human-computer interaction measures.

(Method 1) In one example embodiment, the data processing system includes a detection system for dyslexia, listed as a specific learning disorder having a neurological origin (1), characterized by difficulties with accurate and/or fluent word recognition and by poor spelling.

(Method 1) Input into the present method was a large corpus of errors made by people with dyslexia in reading and writing tasks. Then, a game was created with activities with progressing levels of difficulty by leveraging theory of linguistic and visual tasks that are known to be difficult for people with dyslexia. Finally, these activities implemented into a web-based game that people can play called "Dytective", name in short for representing the data processing system.

(Method 1) The design of the data processing system is based on (i) the empirical linguistic analysis of the errors that people with dyslexia make, (ii) principles of language acquisition, and (iii) specific linguistic skills related to dyslexia. Experiments with 4,335 participants (763 with dyslexia diagnoses) collecting human-computer interaction measures while the participants played to a linguistic based computer game. The data collected was enough to train a neural network model that is able to predict with 91.97% accuracy.

(Method 2) This document presents a method which uses data from human computer interaction and machine learning to predict a neurological deficit. In one embodiment, a statistical model to classify readers with and without dyslexia using a machine learning classifier (e.g., a support vector machine binary classifier), was developed together using eye tracking measures. It is worth noting that the method is independent from the learning algorithm employed.

(Method 2) The model was trained and evaluated in a 10-fold cross experiment with a dataset composed of 1,135 readings of people with and without dyslexia that were recorded with an eye tracker. The method described herein reaches 80.18% accuracy using the most informative features, and can detect individuals with or at risk of neurodevelopmental specific learning disorders. The method has the advantage of having the potential of detecting such a neurodevelopmental specific learning disorder, such as dyslexia, using a computer application, thus making dyslexia detection scalable and inexpensive.

(Method 2) Human-computer interaction studies that use eye tracking with people with dyslexia have normally focused in finding the most accessible text presentations [53, 54]. Again, differences between people with and without dyslexia were found. Even if eye tracking measures have already been used to predict where people tend to look [39] or to improve the interface design of search engines [35], among others. The data processing system described herein can detect dyslexia using eye tracking measures in combination with machine learning.

(Method 3) Mouse movements have been used for many purposes such as understanding web usability, ranking websites readability or content engagement. However, to the best of our knowledge mouse tracking measures have never been used in combination with machine learning to predict dyslexia. Using a with-in subject design with 323 participants, we collected the mouse tracking measures they produced while reading a text on-line. A model, based on a Support Vector Machine binary classifier, reaches 73.43% accuracy using the most informative features. To the best of our knowledge, this is the first time that mouse tracking measures are used to predict automatically readers with dyslexia using machine learning.

(Method 1, 2 and 3) In some implementations, the data processing system includes a feature classification engine that generates classification metrics for a feature vector by performing operations comprising: generating, based on received data representing one or more interactions with a graphical user interface rendered on a client device, the feature vector, with the feature vector comprising features representing one or more features that are indicative of dyslexic behavior; determining, using machine learning logic, a classification metric for each feature of the feature vector; and a prediction engine that generates a prediction value indicative of a predicted likelihood of dyslexia by performing operations comprising: assigning to each feature, based on the classification metric of the respective feature, a prediction weight; and determining the prediction value based on prediction weights for remaining features of the feature vector.

(Method 1, 2 and 3) In some implementations, the data processing system includes a display engine that generates data for the graphical user interface, with the graphical user interface, when rendered on the client device, displaying: a first visual representation of one or more letters of text that represent a selectable control configured to be activated in response to a visual or auditory prompt; and a second visual representation of one or more letters of text that represent another selectable control configured to be activated in response to a visual or an auditory prompt, wherein the first visual representation is juxtaposed to the second visual representation in the graphical user interface.

(Method 1, 2 and 3) In some implementations, data processing system includes a data repository storing data representing visual representations of each of a library of selectable controls that comprise text and data representing auditory prompts that correspond to the first and second visual representations, wherein the display engine selects, from the data repository, data representing the first visual representation and data representing the second visual representation based on a cognitive skill that is being evaluated by the data processing system.

(Method 1, 2 and 3) In some implementations, the feature classification engine receives, from the client device, the data representing one or more interactions with the graphical user interface rendered on the client device.

(Method 1) In some implementations, the graphical user interface represents a computerized game. In some implementations, a feature of the feature vector represents a performance measurement for a computer game that requests input and measures received input. The performance measurement for the computer game comprises one of a click rate measurement, a click delay measurement, a click accuracy measurement, an overall score measurement, and a miss rate measurement. In some implementations, a feature of the feature vector represents a demographic of a user of the client device.

(Method 2) In some implementations, a feature of the feature vector represents one or more measurements of eye movements of a user of the client device as the user reads text rendered on an interface of the client device. In some implementations, the one or more measurements of eye movements comprise one or more of: a mean of values representing eye fixation durations, a number of measured eye fixations, a mean of saccadic movement, number of saccadic movements, sum of saccadic movements, a sum of values representing eye fixations, a number of gaze visits to a specified area on the graphical user interface, and a mean time of values representing gaze visits. In some implementations, a feature of the feature vector represents one of: a designation of a font of displayed text, and a font rating.

(Method 1, 2 and 3) In some implementations, the machine learning logic comprises neural network logic. The actions include a feature transform logic engine that is configured to normalize each feature of the feature vector for use by the machine learning logic.

(Method 3) In some implementations, a feature of the feature vector represents a performance measure for mouse-tracking movements. The performance measure mouse-tracking comprises one of: mean of mouse fixation, number of mouse fixations, sum of mouse fixations, mean of saccadic movement, number of saccadic movements, sum of saccadic movements, and a number of mouse visits to an area of interest.

BRIEF DESCRIPTION OF THE DRAWINGS

FIG. 3 shows examples of user interfaces.
FIG. 4 shows example classification values for various features.
FIG. 5 shows example classification metrics for various features.

DETAILED DESCRIPTION (Method 1, 2 and 3) The data processing system describes a scalable early detection system and method via machine learning models that predict reading and writing difficulties by recording how people interact with a linguistic web-based game, representing a wide variety of human-computer interaction measures.

Figure 1:
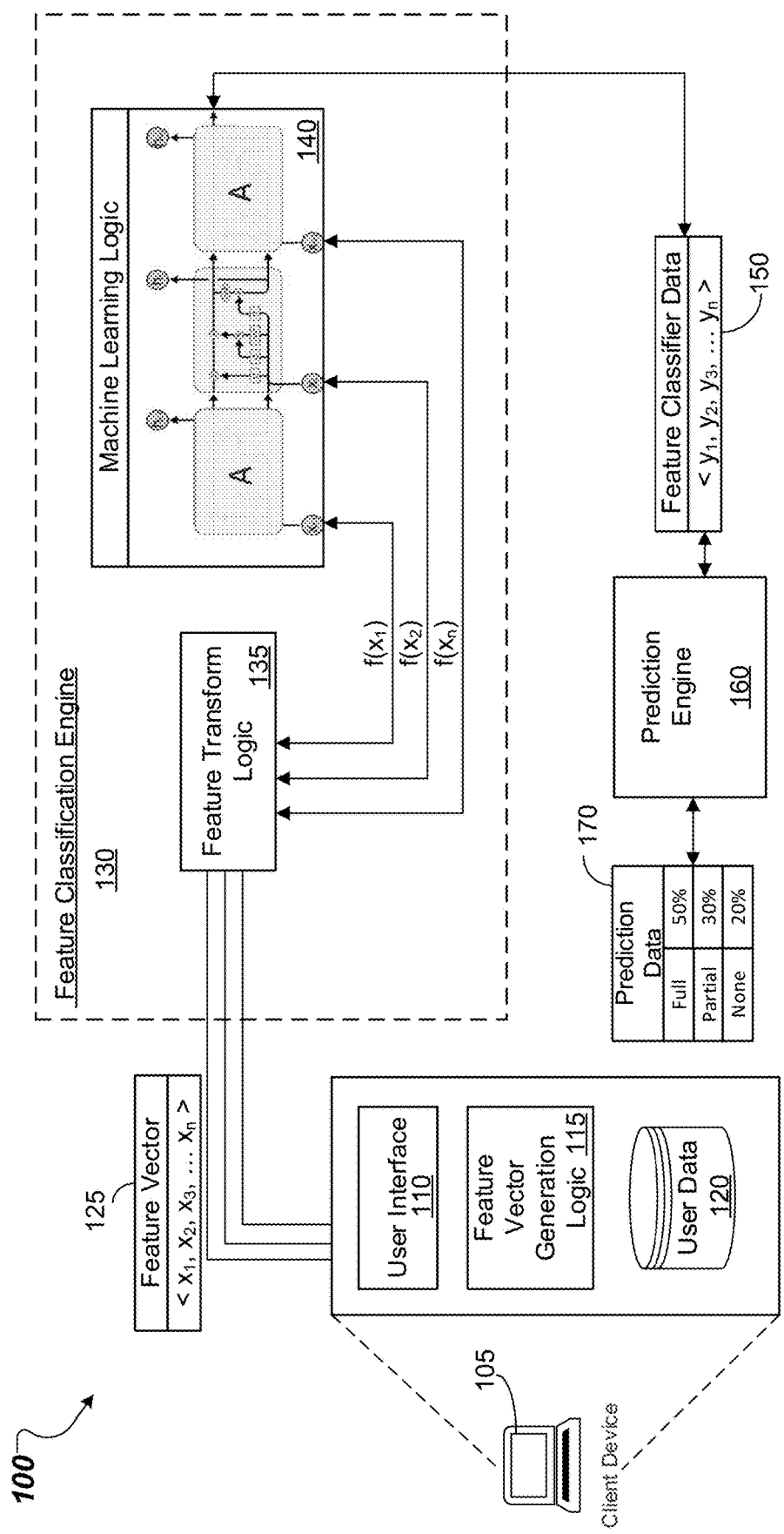
FIG. 1 shows an example data processing system.

FIG. 1 shows an example of the data processing system 100. The data processing system includes a feature classification engine 130 and a prediction engine 160. The feature classification engine 130 and the prediction engine 160 are in communication with each other and with a client device 105.

The client device 105 is configured to display to the user, such as on a hardware interface, a user interface 110 with which a user can interact. Examples of the user interface are described in relation to FIGS. 2-3. The user interface provides a feedback mechanism for the user. The data processing system 100 processes these inputs to determine features (e.g., parameters) that are indicative of the user's interaction (e.g., performance) with the user interface 110. The client device 105 stores user data 120, such as demographic data, etc., which can be input into the feature vector generation logic 115.

The interactions with the interface are represented by the features of a feature vector 125. The feature vector concisely represents the characteristics of the interactions for a particular user, and can be processed by the data processing system, such as using a neural network or other machine learning. The feature vector 125 is generated using feature vector logic 115. The feature vector logic 115 reads the inputs of selected controls (or of measured eye-tracking or mouse-tracking data, such as described below) and transforms the raw input data into a formatted vector that represents the performance of a user in the experiment.

The feature vector 125 is sent from the client device to the feature classification engine 130 of the data processing system 100. The feature classification engine 130 include logic that transforms the feature vector 125 into feature classification data 150 that can be used to make predictions for dyslexia for the user by the prediction engine 160. The feature classification engine includes a feature transform logic engine 135 and machine learning logic 140.

The feature transform logic 135 transforms the feature vector into inputs for the machine learning logic 140. For example, the feature transform logic 135 can normalize the features of the feature vector 125 to values that can be recognized by the machine learning logic 140, such as activation inputs for a neural network. In some implementations, the machine learning logic is a support vector machine. In some implementations, the features of the feature vector are transformed into values between 0 and 1 through a non-linear transformation, where the normalized value represents an activation level for the neural network, and where the normalized scale is a non-linear representation of the values of the features before the normalization process. The values to which the features are transformed can depend on a type of machine learning logic being used, and the weighting scheme associated with the machine learning logic.

The machine learning logic 140 (e.g., a neural network, support vector machine, etc.) receives the normalized features of the feature vector 125 and computes classification data 150, such as through a deep learning process. For example, neural network logic can include a long short-term memory neural network, which tracks dependencies between features of the feature vector 125. Other recurrent neural networks can be used. Other machine learning classifiers can be used as well.

The feature classifier data 150 includes classification metrics for one or more of the features of the feature vector 125 to values for known dyslexic behavior, such as from a feature library. For example, the percentage classification can be computed for each feature. The prediction engine 160 can compare classification values of feature classifier data 150 to a threshold classification, and discard features with insufficient classification. Since features can have dependencies on one another, the classification metrics are determined before features are discarded.

In some implementations, the classification metric values can be stored in a feature index. The index shows the classification values for each feature of the index. The prediction engine 160, using the classification values, generates prediction data 170 representing one or more prediction values for classes of dyslexia. If a prediction value is above a predetermined threshold, the prediction engine 160 predicts that the user has dyslexia. For example, the predetermined threshold can be a prediction value above 50%. In some implementations, to reduce false positives or false negatives, the predetermined threshold can be a higher percentage or a lower percentage than 50%.

Figure 2:
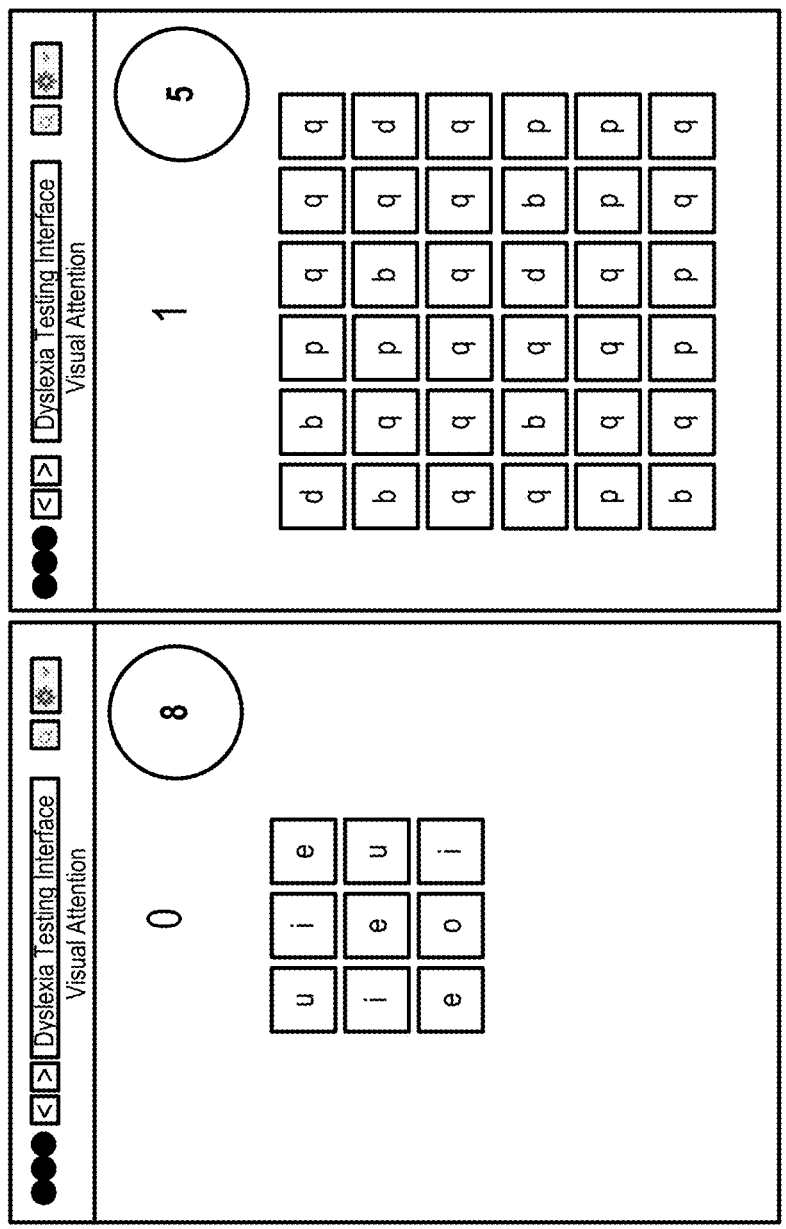
FIG. 2 shows an example of a user interface.

FIG. 2 illustrates one example of the data processing system as a web-based game designed to detect dyslexia in an affordable and scalable way. Players complete linguistically motivated activities designed to reveal differences between people with and without dyslexia. The game includes a first stage in which players hear a character that they should click, e.g., and then click that letter as many times as possible within a time limit. Distractor characters are chosen to be particularly difficult for people with dyslexia to differentiate. FIG. 2. shows example screenshots of first (left) and last (right) exercises of Stage 1, illustrating one way that difficulty is increased progressively.

For example, the user interface 200 of FIG. 2 shows a first visual representation of one or more letters of text. Portions of the text, such as a single letter, multiple letters, words, etc. can represent selectable controls to be activated. For example, a visual or auditory prompt can be sent to the user, such as to select controls representing a particular letter of the text on a screen. The user can select the corresponding controls. The data processing system 100 records the features associated with this interaction, such as the accuracy of the selections, elapsed time, etc., as described below.

The one or more controls of the user interface 200 can be juxtaposed with additional controls included a second representation of one or more letters. The letters can be similar, such as to cause a dyslexic user to hesitate or incorrectly select a control in response to a visual or auditory prompt. The score can be related to a computerized game, such as to select as many correct controls in a permitted amount of time, and so forth.

FIG. 3 shows example stages 300 for the linguistic and attentional abilities targeted by each stage in the data processing system. The 17 stages are split into 32 levels consisting of 212 exercises in total. The games being displayed on the user interface 200 can change depending on the cognitive skill being tested by the data processing system. For example, producing many symbols simultaneously can test pattern recognition abilities, while a matching game can test memory of a user.

A data engine can select a stage, including one or more particular controls, based on the cognitive ability to be tested. In some implementations, the data processing system can dynamically determine which stages to present to a user based on prior performance. For example, in some implementations, the order or content of stages is altered, such as to conduct a new experiment.

FIG. 4 shows data depicting the accuracy of the classifiers in the cross validation experiment, using the optimized feature set and only the features from a particular stage (left) and using all features but the ones of the particular stage (right).

FIG. 5 shows the accuracy of the classifiers in the cross validation experiment, using the optimized feature set and the ablated conditions in which all the features from a particular Stage are removed. The last row shows the result in which all the stages are included. Every feature was necessary to achieve the highest accuracy rate.

Figure 6:
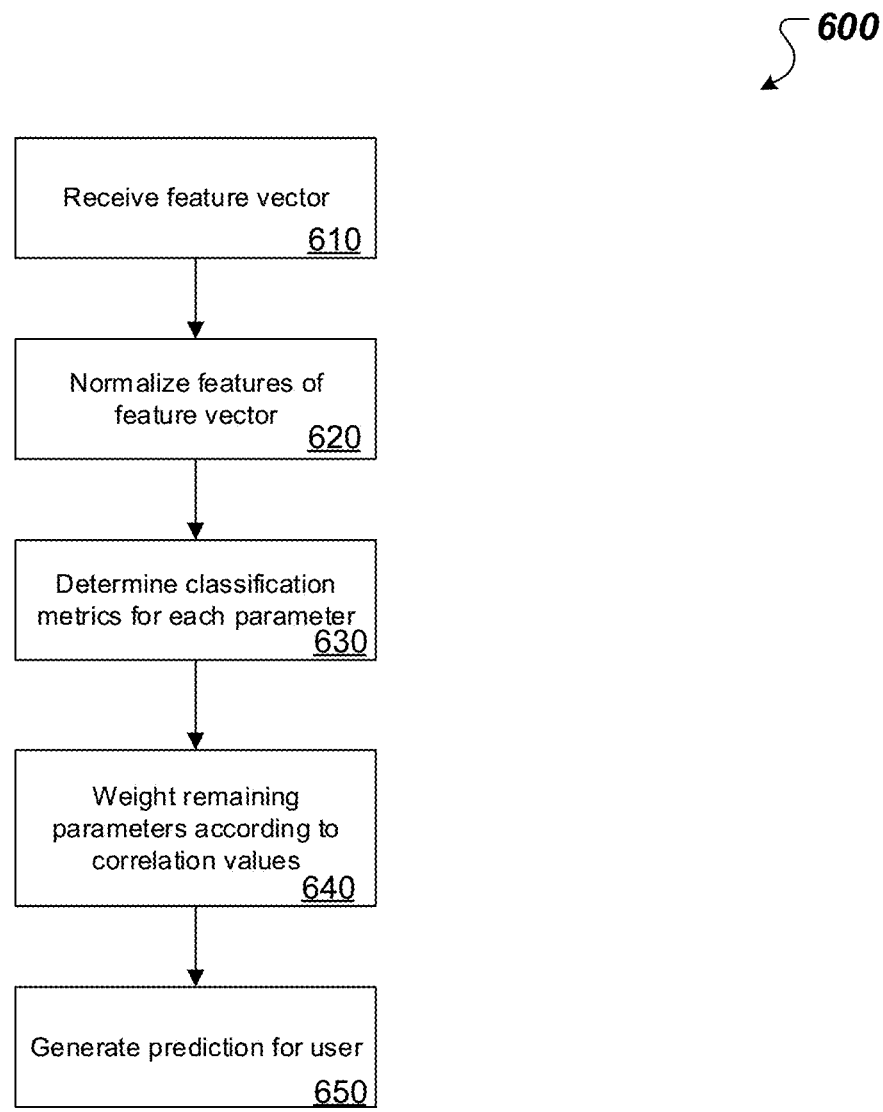
FIG. 6 shows a flow diagram.

FIG. 6 show a flow diagram including an example process for predicting dyslexia by the data processing system. The data processing system receives a feature vector (610), such as a vector comprising one or more of the measured features from an interface. The data processing system normalizes (620) the features of the received feature vector. The normalized features are for the machine learning component of the data processing system. For example, the normalized features can be used as activation inputs for different layers of a neural network system. In some implementations, the neural network system is a long short-term memory neural network. The data processing system can use machine learning logic (e.g., an LTSM neural network component) to determine (630) a classification metric for one or more (e.g., each of) the features of the feature vector. Features are weighted (640) depending on the classification value of the classification metric if the feature meets a minimum threshold. The data processing system generates (650) a prediction of dyslexia for the user.

In a preferred embodiment of the data processing system, the system is configured for dyslexia detection. The data processing system targets linguistic and attention abilities associated with having dyslexia. Players proceed through a series of timed stages composed of linguistic exercises of increasing difficulty. Detection is possible when people with dyslexia perform differently than those without dyslexia. To increase the likelihood of this happening, the exercises were designed using a corpus of real errors produced by people with dyslexia that were previously collected.

Therefore, people with dyslexia will make more errors, and thus the data processing system will be able to differentiate such patients and predict dyslexia for those patients. The goal for the system's users is to solve as many linguistic problems as possible within a time limit.

(Method 1) For instance, in Stage 1, players hear a letter and then click it as many times as possible within the time limit (FIG. 2). After each click, the board changes, and the player receives points if they chose the correct option.

In one implementation, the game has 17 stages, split into 32 levels consisting of 212 exercises in total. Each stage targets a different linguistic or attentional skills and all together aim to cover the maximum potential indicators of dyslexia that could be identified via a computer-game. The exercises are intended for 7-year old users and older.

Most approaches to diagnosis are based on reading and writing measures such as the number of words read per minute or comprehension of written material. The data processing system uses linguistic and attentional exercises designed to distinguish populations with and without dyslexia. Empirical analyses show that errors made by people with dyslexia are different from the errors made by people without dyslexia and that they reflect their difficulties [23]. Hence, the criteria for the linguistic exercises were built on the basis of an analysis of an existing resource of errors made by people with dyslexia [19].

(Method 1) The errors were analyzed from a visual point of view (shapes and visual features shared by the letters of other linguistic segments involved in the errors) and from a linguistic point of view, taking into consideration all the language levels that were involved in the errors, mainly, phonetic, phonologically, morphologically and syntactic levels. The most frequent linguistic and visual features shared in the errors were incorporated into the exercises, as described below.

(Method 1) Manually, different kinds of exercises were created to cover the maximum number of linguistic and attentional abilities related to dyslexia and whose performance can be identified via a computer-based game. Table 1 presents the cognitive skills that each exercise type targets (all the exercises can be grouped in 17 types of exercises or stages). Most of the exercises address phonological awareness because that meta-cognitive skill is the primary factor in solving reading and spelling problems, also in the case of dyslexia [4, 13]. Indirectly, all the exercises target visual attention skills which have been found to have a causal relationship with reading acquisition in the case of dyslexia [9].

(Method 1) The exercises of get progressively more difficult both in later stages and within each stage [11]. Each stage is composed of a number of exercises, ranging from four to twenty-six exercises and they are ranked by their difficulty. The linguistic input of the exercises, e.g., letters, syllables, etc., were selected using both linguistic patterns extracted from our error analysis, and the order in which the linguistic elements and structures are naturally acquired [18]. Thus, exercises that appear earlier should be those that are easiest for people with dyslexia to complete, and should also be those that are easiest for younger children to complete.

(Method 1) In higher difficulty levels, the target letter, syllable, or word(s) tends to be less frequent, longer, has a more complex morphology, and has a higher phonetic and orthographic similarity with other words. Both, error analyses and previous literature show that phonetic and orthographic similarity makes it more challenging for people with dyslexia as together with frequency, length, morphological complexity.

(Method 1) At Stages 1 to 5 the player hears a letter and needs to map it to its visual representation (Stage 1), recognize letters by sound, not letter names (Stage 2), map the syllable they hear with what they see (Stage 3) or recognize words and non-words, respectively (Stages 4 and 5). Exercise complexity is added gradually; higher levels gradually include distractors that share more phonetic features or visual features with the target.

(Method 1) In Stage 6 players are presented with a number of letters and need to spot the one that is different (Visual Attention). Distractors gradually become more phonetically and orthographically similar (Table 1).

(Method 1) In Stages 7 to 12 players must produce correct words by fixing errors based on the real errors that people with dyslexia make. These exercises target Phonological Awareness at a lexical (word) level. They were designed based on the type of errors that appear in texts written by people with dyslexia, such as addition of letters, *arround (around) (Stage 7); omission of letters, *emty (empty); substitution of letters, *scholl (school); transposition of letters, *littel (little); and word boundary errors such as split words, *mis understanding (misunderstanding), and run-ons, *alot (a lot). Depending on the fixing operation the exercises are grouped in following stages. Stage 7 (Insertion of a letter); Stage (Substitution of a letter); Stage 9 (Reordering letters; Stage 10 (Reordering syllables); Stage 11 (split a string of characters into words) and Stage 12 (Deletion of a letter)

(Method 1) At Stages 13 and 14 the player needs to spot written errors in sentences. The reason why these exercises were included is because one of the main challenges that people with dyslexia face is that they do not consciously detect errors while reading [3]. Real word errors were used (correctly spelled words that are not the one the user intended to write, i.e. a letter *form you instead of i.e. a letter from you). In Stage 13 the errors occur in lexical words (Lexical words are content words, i.e. nouns, verbs, adjectives and most adverbs. They have a lexical meaning in contrast with the grammatical meanings expressed by function words, such as prepositions or conjunctions) and in Stage 14 in function words (function words are words that have little lexical meaning, but instead serve to express grammatical relationships with other words within a sentence, such prepositions, pronouns, or conjunctions). This way each of the group of exercises aim at different comprehension language levels and linguistic skills, Syntactic Awareness and Semantic Awareness, respectively. This differentiation was made because lexical and function words are processed differently [18].

(Method 1) At Stage 15 the user needs to memorize sequences of letters with increasing difficulty (Visual Memory & Working Memory). That is, increasingly the sequence to remember contain letters that are less frequent, orthographically less transparent, (Letter whose sound correspondence is not straightforward, that is, letters that can correspond to different sounds depending on the context, for instance, letter c can be pronounced as /k/ in casa, 'house' or as /θ/ in cereza, 'cherry') and share visual and phonetic features among each other.

(Method 1) Finally, at Stages 16 and 17 measure the writing performance and the Phonological Memory via Word and Non-Word Dictation. The criteria to select the words and the non-words are same for the rest of the Stages. For instance, the first exercises start with lexically simpler non-words, i.e. tada while in the higher levels the player is asked to write *mabadana* whose letters are more likely to be mistaken by people with dyslexia according to an empirical analyses of errors, because they share phonological and visual features.

(Method 1) Since text presentation significantly impacts the text readability of people with dyslexia black text on a white background was used, a large font size (minimum 18 points) and the monospaced Courier font face, which benefits both populations with and without dyslexia [2].

(Method 1) In one example embodiment of the data processing system, a web based game written in HTML5, CSS and JavaScript with a backend PHP server and a database. By using these web technologies, it is possible to play game on different devices such as desktops, tablets, and mobile phones. It was implemented with a high level abstraction to make it easily portable to native iOS or Android application for future implementations.

(Method 1) A study with 4,335 participants (763 with diagnosed dyslexia) was conducted using a within-subject design. The goal of the study was to collect data needed to run a machine learning experiment to find out if error-based linguistic problems can predict dyslexia in Spanish. All of the participants played all stages of the game over 15 minutes, but may not have advanced through all of the exercises in each stage.

(Method 1) Participants with dyslexia were recruited through a public call that specialized centers of dyslexia and Hispanic dyslexia associations distributed to their members; the inclusion criterion was to present a dyslexia diagnosis performed by a registered professional. Participants without dyslexia were recruited through school participation and were children who have never presented language problems in their school records. All the participants' first language is Spanish.

(Method 1) The participants with dyslexia consisted of 763 people (393 female, 370 male). Their ages ranged from 7 to 68 (M=17.62, SD=13.35). The group of participants without dyslexia was composed of 3,572 people (1836 female, 1736 male), ages ranging from 7 to 75 (M=12.64, SD=8.37).

(Method 1) To quantify performance, the following dependent measures extracted for each group of exercises was used: (i) Number of Clicks per stage; (ii) Hits, i.e. number correct answers; (iii) Misses, i.e. number in correct answers; (iv) Score i.e. sum of correct answers per group of exercises; (v) Accuracy defined as the number of Clicks divided by the number of Hits; (vi) Missrate defined as the number of Clicks divided by the number of Misses.

(Method 1) An announcement of the study was sent to the main associations of dyslexia of Hispanic countries and countries with large Spanish speaking populations, mainly Argentina, Chile, Mexico, Spain and the USA. The call was also sent to specialized centers that support people with dyslexia. Interested potential participants replied, and after the participation requirements were checked (age, mother languages and technical requirements) and a date was set up to supervise the study. A meeting was scheduled with the participants (and their parents in case the participant was underage) online or by telephone. After they signed the online consent and/or parental consent providing them specific instructions and they completed the study. Parents were specifically warned that they could not help their children to play the game and were asked again afterwards to double check.

(Method 1) 57 schools and 25 specialized center collaborated in the study. For these cases the parental consent was obtained in advance and the study was supervised by the school counselor and the therapist respectively. It was deliberately carried out the study in three different settings (home, school and a specialized center) so the results are independent of the settings.

(Method 1) The dataset is composed of 197 features per participant. From the dataset the data processing system extracts the following features, marked as D if the participant has dyslexia, N if not, and M (maybe) if the participant suspects that he or she has dyslexia but is not diagnosed. Examples include:

(Method 1) [Feature 1] Age of the participant ranging from 7 to 70 years old.

(Method 1) [Feature 2] Gender of the participant, a binary feature with two values female and male.

(Method 1) [Feature 3] Second mother language in case of bilingualism; all the participants had Spanish as mother language.

(Method 1) [Feature 4] Spanish subject. This is a binary feature with two values, yes when the participant has ever failed Spanish subject at school and no when the participant have never failed that subject among all the school history.

(Method 1) [Features 5-197] Performance measures. These features correspond with the six dependent measures (Clicks, Hits, Misses, Score, Accuracy, and Missrate) gathered per level played (32 levels), that is, 192 performance features corresponding to different cognitive skills (see Table1).

(Method 1) Some of the features have numeric (real or integer) values, so ranges for each of them were established to discretize the data by the population median.

(Method 1) In order to find out whether it is feasible to detect people with dyslexia after interacting with the system, a machine learning experiment was set up. Machine learning is the scientific discipline that studies algorithms that can learn from data and make predictions. The output of a machine learning algorithm is called a model, which is capable of making predictions given unseen data. In this case, the goal is to predict whether someone has dyslexia or not based on the data collected while participants used the data processing system.

(Baseline of Method 1 with a subset of the dataset) The binary classifier LIBSVM [6] was used in the polynomial Support Vector Machine (SVM) set-up. A SVM is a method for supervised learning that analyzes data and recognizes patterns for classification. Given a set of training examples, each marked as belonging to a category (in the present case either having dyslexia or not), an SVM training algorithm builds a model that assigns new examples into the categories. When there is an input for the classifier it tries to assign a category to the input and then this is the classification output. This SVM is trained on datasets like the one described in the Dataset Section, and it is able to perform predictions on new participants that may play the data processing system.

(Baseline of Method 1 with a subset of the dataset) A cross validation experiment was performed by dividing the dataset in 243 different subsets having only one participant each. Then a statistical model was iteratively trained on all the data but one participant (242 participants) and tested the one held out. At the end, all the data were tested independently. The participants marked as M (maybe) are used for training the models as if they are D (participants with dyslexia) but they are not used for evaluation. This means that regarding the 212 participants to test, and each model was trained, a total of 212 models, with 242 experiments performed by participants.

(Baseline of Method 1 with a subset of the dataset) The initial results suggest that the model is able to predict people for having or not having dyslexia quite accurately with a final result of 81.60% in the cross-validation experiment by using all features (151 performance features extracted from the game, plus age, gender, mother language and school performance), meaning that the statistical models are able to make a correct prediction in 173 of the 212 participants.

(Baseline of Method 1 with a subset of the dataset) In order to improve performance, a feature selection experiment was carried out following a backward algorithm. The start was testing a model with all features, and iteratively remove features one by one by training new models; if the performance was better or equal than before it was permanently removed the feature from the feature set, seeking more informative features.

(Baseline of Method 1 with a subset of the dataset) After it was partially reduced the feature set, and a redundancy selection experiment was carried out, in which the features were removed in pairs, by testing all possible combinations in a double loop, meaning that a particular feature was fixed and it started removing all feature plus the particular feature that were fixed before. If the performance is better or equal than before the data processing system removes the pair of features from the feature set.

(Baseline of Method 1 with a subset of the dataset) After the optimization round an improved result of 85.85% was obtained, which increases the previous score substantially and reduces the number of features, from 198 to 150. Some of the dependent measures from some Stages were left out, such as the number of Clicks in Stage 4. The model selected features from all the stages. The model is now capable of correctly predicting the condition of 182 of the 212 participants.

(Method 1) The data processing system comprises a machine learning model, such as a long short-term memory (LSTM) neural network, trained on data that is able to classify people as having a neurodevelopmental-specific learning disorder, such as dyslexia, with high accuracy. This section describes the utility of the different features used and discuss the errors made by the model.

(Method 1) With bidirectional-LSTMs the model reaches and accuracy of 91.97% (149 correct instances of 162) when it is evaluated in the held-out test set. For the dyslexic class the precision is 1 and the recall is 0.48, which gives an F-measure of 0.64. For the non-dyslexic class, the precision is 0.91, the recall is 1 and the F-measure is 0.95.

(Method 1) The first conclusion to extract is that the model is capable of detecting the risk of having dyslexia regardless of the distribution of people that are included in the dataset. Of course, better results are expected if the size of the training set is increased.

(Method 1) The data processing system includes a system which allows for detection of neurodevelopmental-specific learning disorder, including but not limited to dyslexia and, "Dytective" presents a number of opportunities for improving lives of people with dyslexia. The data processing system can be used to detect dyslexia with students who have not yet been diagnosed. The system can be applied to other languages, such as but not limited to English and German, and will enable new ways to estimate the prevalence of dyslexia among web users, which is a long-standing challenge. The data processing system can screen dyslexia in Spanish while applying machine learning to measures extracted from linguistic and attentional exercises designed on the basis of generated content by people with dyslexia.

(Method 2) The dataset is derived from an eye tracking experiment with 97 subjects with normal or corrected-to-normal vision; 48 of them with diagnosed dyslexia. The participants with dyslexia (22 female, 26 male) presented a confirmed diagnosis of dyslexia. Their ages ranged from 11 to 50 (x=20.96, s=9.98). Except from 3 participants, all of the participants were attending school or high school (26 participants), or they were studying or had already finished university degrees (19 participants). The group of participants without dyslexia was composed of 49 people (28 female, 21 male). Their ages ranged from 11 to 54 (x=29.30, s=9.03). Except from 5 participants, the rest were either attending or had finished school or high school (17 participants) or university (27 participants).

(Method 2) This data was derived from a within-subject design experiment. Each participant read 12 different texts with 12 different typefaces. The texts and the fonts were counter-balanced to avoid sequence effects. Therefore, the data with respect to text-font combinations was evenly distributed.

(Method 2) The twelve fonts include: Arial, Arial Italic, Times and Times Italic—the most common fonts used on screen and printed texts, respectively—; OpenDyslexic and OpenDyslexic Italic—designed specifically for people with dyslexia—; Verdana, recommended by the British Dyslexia Association; Courier—the most common example of monospaced font—; Helvetica and Myriad—broadly used in graphic design and typeface of choice of Microsoft and Apple, respectively —; Garamond—for its strong legibility for printed materials— and CMU—widely used in scientific publishing, as is the default of the typesetting program TeX, as well as a free typeface supporting many languages.

(Method 2) The readings of each text were recorded using eye tracking, the user preferences towards the fonts were gathered using questionnaires with five-point Likert scales. Comprehension questions were presented at the end of each text as a control variable.

(Method 2) The text used in the experiments met comparability requirements. They were extracted from the same book, Impostores ('Impostors'), by Lucas Sanchez. They all had the same genre and same style; the same number of words (60 words); similar word length, with an average length ranging from 4.92 to 5.87 letters; absence of numerical expressions, acronyms, and foreign words, because people with dyslexia especially encounter problems with such words [30]. The text presentation was also controlled, except from the typeface. All the texts were left-justified, using a 14 points font size, and the column width did not exceed 70 characters/column, as recommended by the British Dyslexia Association. The color used was the most frequently used in the Web for text: black text on white background.

(Method 2) The equipment used was the eye tracker Tobii 1750, which has a 17-inch TFT monitor with a resolution of 1,024×768 pixels. The time measurements of the eye tracker have a precision of 0.02 seconds. Hence, all time values are presented in the dataset with an accuracy of two decimals. The eye tracker was calibrated individually for each participant and the light focus was always in the same position. The distance between the participant and the eye tracker was constant (approximately 60 cm. or 24 in.) and con-trolled by using a fixed chair.

(Method 2) While one example embodiment using eye-tracking, other Human Computer Interaction measures to improve the accuracy of the model and to address younger population (non-readers) to detect literacy disorders at risk can be employed. Some of these measures include but not limited to, other eye-tracking measures, mouse tracking, mouse movements, head tracking, touch tracking, multi-touch tracking, and face recognition, emotion recognition, and performance in virtual reality. All of these measures are used in relationship with reading performance—such as reading speed, reading accuracy, letter/symbols/sound/words recognition, phonological, syntactic and semantic awareness, comprehension, among others— writing performance—including visual memory, copy, dictation, typing accuracy, typing efficiently, among others—, visual-spatial skills, memory, and other executive abilities. For more details about the experimental design on how these readings were collected, please refer to [53].

(Method 2) Therefore, our dataset is composed of readings marked as D if the participant has dyslexia and N if not, there are 12 readings per participant, that is 1,164 readings; 29 of these readings were not properly recorded with not a number values. Hence, the data processing system removed those readings from the dataset having a final dataset containing 1,135 readings. From the dataset the data processing system extracted the following features:

Age of the participant, ranging from 11 to 54 years old.
Typeface: One of the 12 typefaces used for the text.
Italic: This is a binary feature with two values, italic when the text had an italic type and roman when the text had a roman type.
Serif: This is a binary feature with two values, sans serif when the font of the text had a typeface without serf—Arial, Helvetica, Myriad, and Verdana—, and serif when the text had typefaces with serif—CMU, Garamond, and Times—.
Typeface designed for dyslexia: A binary feature that shows when the font in the text had a typeface specifically designed for people with dyslexia.
Typeface preference of the participant: Value given to a typeface by the participant using a five-point Likert scale.
Number of visits: Total number of visits to the area of interest.
Mean of visit: Duration of each individual visit within the area of interest (the text).
Sum of visits (reading time): Sum of all the visits. This is equivalent to the reading time of the whole text.
Mean of fixation: When reading a text, the eye does not move contiguously over text, but alternates saccades and visual fixations, that is, jumps in short steps and rests over pieces of text. It denotes how long the eye rests still on a single spot of the text.
Number of fixations: Total number of fixations while reading a text per visit.
Sum of fixations: Sum of all fixations.

(Method 2) Some of the features have numeric (real or integer) values, so the data processing system establishes some ranges for each of them to discretize the data. For instance, the age of the participants is divided in 3 different groups: (1) younger than 14 years old, (2) from 14 to 19 years old, and (3) from 20 to 54 years old.

(Method 2) In order to find out whether it is feasible to detect readings of users with dyslexia, the data processing system includes a machine learning component. Machine learning is the scientific discipline that studies algorithms that can learn from data and make predictions. The output of a machine learning algorithm is called a model which is capable of making predictions given unseen data (normally for evaluation). In some implementations, a long short-term memory (LSTM) neural network is used.

(Method 2) The data processing system includes a binary classifier of LIBSVM [29] in the polynomial Support Vector Machine (SVM) set-up. An SVM is a method for supervised learning that analyzes data and recognize patterns for classification. Given a set of training examples, each marked as belonging to a category, an SVM training algorithm builds a model that assigns new examples into the categories. It represents the examples as points in space and classifies them according to hyperplanes. When there is an input for the classifier it tries to assign a hyperplane to the input and then this is the classification output. Our SVM is trained on datasets as the one described in the previous section, and it is able to perform predictions on new readings.

(Method 2) The data processing system performs a 10-fold cross validation experiment by dividing the data in 10 different roughly equal subsets (10% of the data in each subset). In some implementations, the data processing system trains a statistical model on the rest of the data (90%) and tests the corresponding fold by iterating 10 times. The data processing system randomizes the data and stratifies sampling to ensure a similar distribution of data in all folds. In some implementations, the data processing system kept all readings by the same user in the same fold such that each fold includes a similar number of readings marked as participants with and without dyslexia, and that a user does not serve for training a model that will predict readings of the same user. The data processing system thus generalizes the statistical analysis on an independent dataset, such as new readings. In some implementations, the data processing system uses 10-fold cross validation to improve reliability for smaller datasets.

(Method 2) Table 1 shows the accuracy of the support vector machines models for each of the folds. This result suggests that the model is able to predict readings of users with dyslexia quite accurately with a final result of 80.18%, meaning that the statistical models are able to make a correct prediction in 910 of the 1,135 readings.

TABLE 1

Accuracy of the classifiers in the 10-fold cross validation experiment.

| Dataset | Accuracy |
| --- | --- |
| Fold-1 | 83.62% (97/116) |
| Fold-2 | 96.26% (103/107) |
| Fold-3 | 69.90% (72/103) |
| Fold-4 | 89.74% (105/117) |
| Fold-5 | 86.48% (96/111) |
| Fold-6 | 73.15% (79/108) |
| Fold-7 | 61.21% (71/116) |
| Fold-8 | 82.41% (89/108) |
| Fold-9 | 85.47% (100/117) |
| Fold-10 | 74.24% (98/132) |
| All | 80.18% (910/1,135) |

(Method 2) The data processing system uses one or more of the following features for classification: (1) Sum of visits, (2) mean of fixations, and (3) age of the participant. The data processing system is can determine whether some features are useful standing alone, such as (1) number of visits or (2) number of fixations, and determine that such features can be not useful when they are used jointly with the features listed above, such as due to redundancy, as they express the same information. Other features, such as typeface, italic or serif do not affect in the predictions.

(Method 2) The age of the participants can range from 11 to 54 years old. The data processing system is configured to recognize that users with dyslexia tend to improve their reading skills with age. In some implementations, to test this phenomenon, the data processing system is configured to run the same experiment (with the same folds), as in Section 5, by removing the age of the participant as a feature. Table 2 shows the results of the SVM models without considering the age of the participants. The final result is 76.38 of final accuracy (losing 3.8 points). This indicates that the age of the users shows clearer differences in their reading performance. Nonetheless, in the dataset the age average of the participants with dyslexia is 20.96, with a standard deviation of 9.98 while the age average of the participants without dyslexia is 29.20 with a standard deviation of 9.03 [53]. If the ages of both groups were perfectly matched, the data processing system can determine that there are more homogenous results between folds.
(Method 2)

TABLE 2

Accuracy of the classifiers in the 10-fold cross validation experiment without considering the age of the participant as a feature

| Dataset | Accuracy |
| --- | --- |
| Fold-1 | 83.62% (97/116) |
| Fold-2 | 85.98% (92/107) |
| Fold-3 | 65.05% (67/103) |
| Fold-4 | 84.62% (99/117) |
| Fold-5 | 74.77% (83/111) |
| Fold-6 | 72.22% (78/108) |
| Fold-7 | 56.03% (65/116) |
| Fold-8 | 82.41% (89/108) |
| Fold-9 | 85.47% (100/117) |
| Fold-10 | 73.48% (97/132) |
| All | 76.39% (867/1,135) |

(Method 2) The data processing system can determine that some folds achieve higher results than others, being 96.26% the highest and 61.21% the lowest, even when the data processing system performs stratified sampling. For instance, for a participant with dyslexia who is 50 years old and might have already overcome most of its reading issues, the data processing system can classify the participant as a participant with dyslexia. The data processing system can be configured to improve results using additional eye tracking experiments.

(Method 2) The data processing system is configured to predict dyslexia for languages with deeper orthographies such as English, German, Bulgarian, Spanish and so forth. Therefore, dyslexia prediction in other languages using eye tracking measures is feasible, especially in languages with shallow orthographies where reading speed is a strong indicator for diagnosing dyslexia [55, 60]. Furthermore, this method can include other tracking measures of human computer interaction, such as but not limited to, mouse tracking and different types of reading and writing performance.

(Method 2) The data processing system includes a method which enables a feasible, scalable, accurate and cost effective approach to detect individuals with or at high risk of neurodevelopmental specific learning disorders, such as dyslexia.

(Method 3) All the participants read the same text, that is, we used a within-subject design. For quantifying the mouse movements of the participants, we used the following mouse tracking (MT) dependent measures.

Time to First Move: Time that the participant spends before making the first mouse movement. It is measured from the moment that the text is exposed to the participant.

MT Time: Time that the participant moved the mouse.

MT Distance: Total number of pixels travelled by the mouse.

MT Speed: The speed of the mouse is calculated dividing the MT Time by the number of pixels of the MT Distance.

Mean of fixation: The mouse does not move contiguously over text, but alternates saccades and mouse fixations. This measure refers to the mean of the mouse fixation duration over the text.

Number of MT Fixations: Number of fixation of the mouse while reading a text. —Total MT Fixation Time: Sum of all mouse tracking fixations.

Number of MT Saccades: Number of saccadic movements performed by the mouse. A saccadic movement is defined by the movement of the mouse between fixations.

Mean of MT Saccades: The mean distance in pixels of the saccadic mouse movements.

Total fixation time: Total time resulting from the sum of all mouse tracking fixations.

(Method 3) The Table below shows the accuracy of the support vector machines models for each of the folds. This result suggests that the model is able to predict readings of users with dyslexia quite accurately with a final result of 73.44%.

| Dataset | Accuracy |
| --- | --- |
| Fold-1 | 59.36% (19/32) |
| Fold-2 | 71.86% (23/32) |
| Fold-3 | 62.50% (20/32) |
| Fold-4 | 68.75% (22/32) |
| Fold-5 | 75.00% (24/32) |
| Fold-6 | 65.63% (21/32) |
| Fold-8 | 68.75% (22/32) |
| Fold-7 | 87.50% (28/32) |
| Fold-8 | 84.38% (27/32) |
| Fold-10 | 90.63% (29/32) |
| All | 73.44% (235) |

(Method 1, 2, 3) The data processing system used for the operations described in association with any of the computer-implement methods described previously. The data processing system is intended to include various forms of digital computers, such as laptops, desktops, workstations, personal digital assistants, servers, blade servers, mainframes, and other appropriate computers. The data processing system also includes mobile devices, such as personal digital assistants, cellular telephones, smartphones, and other similar computing devices. Additionally, the system includes portable storage media, such as, Universal Serial Bus (USB) flash drives. For example, the USB flash drives may store operating systems and other applications. The USB flash drives include input/output components, such as a wireless transmitter or USB connector that may be inserted into a USB port of another computing device.

(Method 1, 2, 3) The data processing system includes a processor, a memory, a storage device, and an input/output device. Each of the components are interconnected using a system bus. The processor is capable of processing instructions for execution within the data processing system. The processor may be designed using any of a number of architectures. For example, the processor may be a CISC (Complex Instruction Set Computers) processor, a RISC (Reduced Instruction Set Computer) processor, or a MISC (Minimal Instruction Set Computer) processor.

(Method 1, 2, 3) In one implementation, the processor is a single-threaded processor. In another implementation, the processor is a multi-threaded processor. The processor is capable of processing instructions stored in the memory or on the storage device to display graphical information for a user interface on the input/output device.

(Method 1, 2, 3) The memory stores information within the data processing system. In one implementation, the memory is a computer-readable medium. In one implementation, the memory is a volatile memory unit. In another implementation, the memory is a non-volatile memory unit.

(Method 1, 2, 3) The storage device is capable of providing mass storage for the engine 500. In one implementation, the storage device is a computer-readable medium. In various different implementations, the storage device may be a floppy disk device, a hard disk device, an optical disk device, or a tape device.

(Method 1, 2, 3) The input/output device provides input/output operations for the engine. In one implementation, the input/output device includes a keyboard and/or pointing device. In another implementation, the input/output device includes a display unit for displaying graphical user interfaces.

(Method 1, 2, 3) The features described is implemented in digital electronic circuitry, or in computer hardware, firmware, software, or in combinations of them. The apparatus is implemented in a computer program product tangibly embodied in an information carrier, e.g., in a machine-readable storage device for execution by a programmable processor; and method steps is performed by a programmable processor executing a program of instructions to perform functions of the described implementations by operating on input data and generating output. The described features are implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that is used, directly or indirectly, in a computer to perform a certain activity or bring about a certain result. A computer program is written in any form of programming language, including compiled or interpreted languages, and it is deployed in any form, including as a stand-alone program or as a module, component, subroutine, or other unit suitable for use in a computing environment.

(Method 1, 2, 3) Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory is supplemented by, or incorporated in, ASICs (application-specific integrated circuits).

(Method 1, 2, 3) To provide for interaction with a user, the features is implemented on a computer having a display device such as a CRT (cathode ray tube) or LCD (liquid crystal display) monitor for displaying information to the user and a keyboard and a pointing device such as a mouse or a trackball by which the user provides input to the computer.

(Method 1, 2, 3) The features are implemented in a computer system that includes a back-end component, such as a data server, or that includes a middleware component, such as an application server or an Internet server, or that includes a front-end component, such as a client computer having a graphical user interface or an Internet browser, or any combination of them. The components of the system are connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

(Method 1, 2, 3) The computer system includes clients and servers. A client and server are generally remote from each other and typically interact through a network, such as the described one. The relationship of client and server arises by virtue of computer programs running on the respective computers and having a client-server relationship to each other.

Other embodiments are within the scope and spirit of the description claims. Additionally, due to the nature of software, functions described above can be implemented using software, hardware, firmware, hardwiring, or combinations of any of these. Features implementing functions may also be physically located at various positions, including being distributed such that portions of functions are implemented at different physical locations. The use of the term "a" herein and throughout the application is not used in a limiting manner and therefore is not meant to exclude a multiple meaning or a "one or more" meaning for the term "a." Additionally, to the extent priority is claimed to a provisional patent application, it should be understood that the provisional patent application is not limiting but includes examples of how the techniques described herein may be implemented.

A number of exemplary embodiments of the invention have been described. Nevertheless, it will be understood by one of ordinary skill in the art that various modifications may be made without departing from the spirit and scope of the techniques described herein.

REFERENCES

[1] American Psychiatric Association. 2013. Diagnostic and statistical manual of mental disorders, (DSM-V). American Psychiatric Publishing, Arlington, VA.

[2] British Dyslexia Association. 2012. Dyslexia Style Guide. (January 2012). http://www.bdadyslexia.org.uk/.

[3] Maggie Bruck. 1988. The word recognition and spelling of dyslexic children. Reading Research Quarterly (1988), 51{69.

[4] Maggie Bruck. 1992. Persistence of dyslexics' phonological awareness deficits. Developmental psychology 28, 5 (1992), 874.

[5] Manuel Carreiras, Andrea Mechelli, and Cathy J. Price. 2006. Effect of word and syllable frequency on activation during lexical decision and reading aloud. Human brain mapping 27, 12 (2006), 963{972.

[6] Chih-Chung Chang and Chih-Jen Lin. 2011. LIBSVM: A library for support vector machines. ACM Transactions on Intelligent Systems and Technology 2 (2011), 27:1{27: 27. Issue 3. Software available at http://www.csie.ntu.edu.tw/~cjlin/libsvm.

[9] Andrea Facoetti, Pierluigi Paganoni, Massimo Turatto, Valentina Marzola, and Gian Gastone Mascetti. 2000. Visual-spatial attention in developmental dyslexia. Cortex 36, 1 (2000), 109{123.

[11] Christopher Cunningham Gabe Zichermann. 2011. Gamification by Design: Implementing Game Mechanics in Web and Mobile Apps. O'Reilly.

[12] Ombretta Gaggi, Giorgia Galiazzo, Claudio Palazzi, Andrea Facoetti, and Sandro Franceschini. 2012. A serious game for predicting the risk of developmental dyslexia in pre-reader children. In Proc. ICCCN'12. IEEE, 1{5.

[14] Heikki Lyytinen, Jane Erskine, Janne Kujala, Emma Ojanen, and Ulla Richardson. 2009. In search of a science-based application: A learning tool for reading acquisition. Scandinavian journal of psychology 50, 6 (2009), 668{675.

[15] Heikki Lyytinen, Miia Ronimus, Anne Alanko, Anna-Maija Poikkeus, and Maria Taanila. 2007. Early identification of dyslexia and the use of computer game-based practice to support reading acquisition. Nordic Psychology 59, 2 (2007), 109.

[17] Saifuddin Mohtaram, Naim Che Pee, and Abdul Samad Sibgatullah. 2014. Mobile Dyslexia Screening Test: A New Approach through Multiple Deficit Model Mobile Game to Screen Developmental Dyslexia Children. In Malaysia University Conference Engineering Technology.

[18] Steven Pinker. 2009. Language Learnability and Language Development. Harvard University Press.

[19] Luz Rello, Ricardo Baeza-Yates, and Joaquim Llisterri. 2014. DysList: An Annotated Resource of Dyslexic Errors. In Proc. LREC 2014. Reykjavik, Iceland, 1289-1296.

[20] Francisca Serrano and Sylvia Defior. 2008. Dyslexia speed problems in a transparent orthography. Annals of Dyslexia 58, 1 (2008), 81-95.

[22] Sally E. Shaywitz. 2003. Overcoming dyslexia: A new and complete science-based program for reading problems at any level. Knopf.

[23] Christopher. Sterling, Marion. Farmer, Barbara. Riddick, Steven. Morgan, and Catherine. Matthews. 1998. Adult dyslexic writing. Dyslexia 4, 1 (1998), 1-15.

[24] Elise Temple, Gayle K. Deutsch, Russell A. Poldrack, Steven L. Miller, Paula Tallal, Michael M. Merzenich, and John de Gabrieli. 2003. Neural deficits in children with dyslexia ameliorated by behavioral remediation: evidence from functional MRI. Proceedings of the National Academy of Sciences 100, 5 (2003), 2860-2865.

[25] Lieven Van den Audenaeren, Veronique Celis, Vero Vanden Abeele, Luc Geurts, Jelle Husson, Pol Ghesquiere, Jan Wouters, Leen Loyez, and Ann Goeleven. 2013. DYSL-X: Design of a tablet game for early risk detection of dyslexia in preschoolers. In Games for Health. Springer, 257-266.

[27] Johannes C. Ziegler and Usha Goswami. 2005. Reading acquisition, developmental dyslexia, and skilled reading across languages: a psycholinguistic grain size theory. Psychological bulletin 131, 1 (2005),

[28] D. Adler-Grinberg and L. Stark. Eye movements, scan paths, and dyslexia. *American Journal of Optometry and Physiological Optics,* 55(8):557-570, 1978.

[29] C.-C. Chang and C.-J. Lin. LIBSVM: A library for support vector machines. *ACM Transactions on Intelligent Systems and Technology,* 2:27:1-27:27, 2011. Software available at http://www.csie.ntu.edu.tw/-cjlin/libsvm.

[30] F. Cuetos and F. Valle. Modelos de lectura y dislexias (Reading models and dyslexias). *Infancia y Aprendizaje (Infancy and Learning),* 44:3-19, 1988.

[31] G. F. Eden, J. F. Stein, H. M. Wood, and F. B. Wood. Differences in eye movements and reading problems in dyslexic and normal children. *Vision Research,* 34(10): 1345-1358, 1994.

[32] R. D. Elterman, L. A. Abel, R. B. Daroff, L. F. Dell'Osso, and J. L. Bornstein. Eye movement patterns in dyslexic children. *Journal of Learning Disabilities,* 13(1): 16-21, 1980.

[33] J. Everatt, M. F. Bradshaw, and P. B. Hibbard. Individual differences in reading and eye movement control. *Eye guidance in reading and scene perception, pages* 223-242, 1998.

[34] N. Goulandris, editor. *Dyslexia in different languages: Cross-linguistic comparisons.* Whurr Publishers, London, 2003.

[35] L. A. Granka, T. Joachims, and G. Gay. Eye-tracking analysis of user behavior in www search. In *Proceedings of the 27th annual international ACM SIGIR conference on Research and development in information retrieval,* pages 478-479. ACM, 2004.

[36] M. Grund, C. L. Naumann, and G. Haug. *Diagnostischer Rechtschreibtestfur 5. Klassen: DRT 5; Manual.* Deutsche Schultests. Beltz Test, G"ottingen, 2, aktual. aufl. in neuer rechtschreibung edition, 2004.

[37] J. Hyona and R. K. Olson. Eye fixation patterns among dyslexic and normal readers: Effects of word length and word frequency. Journal of Experimental Psychology: Learning, Memory, and Cognition, 21(6):1430, 1995.

[38] A. W. Inhoff and K. Rayner. Parafoveal word processing during eye fixations in reading: Effects of word frequency. *Perception & Psychophysics,* 40(6):431-439, 1986.

[39] T. Judd, K. Ehinger, F. Durand, and A. Torralba. Learning to predict where humans look. In *Computer Vision, 2009 IEEE 12th international conference on,* pages 2106-2113. IEEE, 2009.

[40] M. A. Just and P. A. Carpenter. A theory of reading: From eye fixations to comprehension. *Psychological review,* 87:329-354, 1980.

[41] H. Lyytinen, J. Erskine, J. Kujala, E. Ojanen, and U. Richardson. In search of a science-based application: A learning tool for reading acquisition. *Scandinavian journal of psychology,* 50(6):668-675, 2009.

[42] H. Lyytinen, M. Ronimus, A. Alanko, A.-M. Poikkeus, and M. Taanila. Early identification of dyslexia and the use of computer game-based practice to support reading acquisition. *Nordic Psychology,* 59(2):109, 2007.

[43] K. Nation, C. M. Marshall, and G. Altmann. Investigating individual differences in childrens real-time sentence comprehension using language-mediated eye movements. *Journal of Experimental Child Psychology,* 86(4): 314-329, 2003.

[44] R. K. Olson, R. Kliegl, B. J. Davidson, and G. Foltz. Individual and developmental differences in reading disability. *Reading research: Advances in theory and practice,* 4:1-64, 1985.

[45] E. Paulesu, J.-F. D'emonet, F. Fazio, E. McCrory, U. Chanoine, N. Brunswick, S. F. Cappa, G. Cossu, M. Habib, C. D. Frith, and U. Frith. Dyslexia: Cultural diversity and biological unity. *Science,* 291(5511):2165-2167, November 2001.

[46] F. J. Pirozzolo and K. Rayner. The neural control of eye movements in acquired and developmental reading disorders. *Studies in Neurolinguistics,* 4:1-27, 1978.

[47] G. E. Raney and K. Rayner. Word frequency effects and eye movements during two readings of a text. *Canadian Journal of Experimental Psychology,* 49(2):151, 1995.

[48] K. Rayner. The role of eye movements in learning to read and reading disability. *Remedial and Special Education,* 6(6):53-60, 1985.

[49] K. Rayner. Eye movements and the perceptual span in beginning and skilled readers. *Journal of experimental child psychology,* 41(2):211-236, 1986.

[50] K. Rayner. Eye movements in reading and information processing: 20 years of research. *Psychological Bulletin,* 124:372-422, 1998.

[51] K. Rayner and S. A. Duffy. Lexical complexity and fixation times in reading: Effects of word frequency, verb complexity, and lexical ambiguity. *Memory & Cognition,* 14(3):191-201, 1986.

[52] K. Rayner and G. E. Raney. Eye movement control in reading and visual search: Effects of word frequency. *Psychonomic Bulletin & Review,* 3(2):245-248, 1996.

[53] L. Rello. DysWebxia. *A Text Accessibility Model for People with Dyslexia.* PhD thesis, Universitat Pompeu Fabra, 2014.

[54] L. Rello and R. Baeza-Yates. Good fonts for dyslexia. In Proc. *ASSETS'13,* Bellevue, Washington, USA, 2013. ACM Press.

[55] F. Serrano and S. Defior. Dyslexia speed problems in a transparent orthography. *Annals of Dyslexia,* 58(1):81-95, 2008.

[56] M. A. Tinker. The study of eye movements in reading. *Psychological Bulletin,* 43(2):93, 1946.

[57] M. A. Tinker. Recent studies of eye movements in reading. *Psychological Bulletin,* 55(4):215, 1958.

[58] W. Tops, M. Callens, J. Lammertyn, V. Van Hees, and M. Brysbaert. Identifying students with dyslexia in higher education. *Annals of dyslexia,* 62(3):186-203, 2012.

[59] J. Toro and M. Cervera. *TALE: Test de An'alisis de Lectoescritura (TALE: Literacy Analysis Test).* Visor, Madrid, 1984.

[60] P. E. Tressoldi, G. Stella, and M. Faggella. The development of reading speed in Italians with dyslexia a longitudinal study. *Journal of learning disabilities,* 34(5): 414-417, 2001.

[61] F. R. Vellutino, J. M. Fletcher, M. J. Snowling, and D. M. Scanlon. Specific reading disability (dyslexia): What have we learned in the past four decades? *Journal of Child Psychology and Psychiatry,* 45(1):2-40, 2004.

What is claimed is:

1. A data processing system for processing a feature vector that comprises one or more features that are indicative of dyslexic behavior, the data processing system comprising:

at least one processor; and a memory storing instructions that, when executed by the at least one processor, causes the at least one processor to perform operations comprising:

receiving, through a camera, data representing measurements of eye movements of a user of a client device as the user reads text rendered on a graphical user interface of the client device;

receiving, through the graphical user interface of the client device, data representing one or more interactions with the graphical user interface of the client device;

generating, based on the data representing one or more interactions with the graphical user interface of the client device and the data representing the measurements of the eye movements, the feature vector, wherein a feature of the feature vector represents one or more measurements of the eye movements of the user of the client device or other data indicative of dyslexic behavior;

determining, using machine learning logic, a classification metric for each feature of the feature vector, the machine learning logic being trained by operations comprising:
  selecting a set of features representing performance measurements for a set of users interacting with user interfaces;
  receiving, for the set of users, label data specifying whether the user is dyslexic;
  training the machine learning logic using the set of features and the label data; and
  iteratively removing one or more features from the set of features until an accuracy of the machine learning logic satisfies a threshold accuracy to generate a final set of features for including the feature vector; and
generating a prediction value indicative of a predicted likelihood of dyslexia for the user by performing operations comprising:
  assigning to each feature of the feature vector, based on the classification metric of the respective feature, a prediction weight;
  determining the prediction value based on that prediction weight for each feature of the feature vector; and
  outputting, for rendering on a display, a representation of the prediction value.

2. The data processing system of claim 1, the operations further comprising:
generating data for the graphical user interface, with the graphical user interface, when rendered on the client device, the graphical user interface displaying:
  a first visual representation of one or more letters of text that represent a selectable control configured to be activated in response to a visual or auditory prompt; and
  a second visual representation of one or more letters of text that represent another selectable control configured to be activated in response to a visual or an auditory prompt, wherein the first visual representation is juxtaposed to the second visual representation in the graphical user interface.

3. The data processing system of claim 2, further comprising:
a data repository storing data representing visual representations of each of a library of selectable controls that comprise text and data representing auditory prompts that correspond to the first and second visual representations,
wherein the operations comprise selecting, from the data repository, data representing the first visual representation and data representing the second visual representation based on a cognitive skill that is being evaluated by the data processing system.

4. The data processing system of claim 1, further comprising receiving, from the client device, the data representing one or more interactions with the graphical user interface rendered on the client device.

5. The data processing system of claim 1, wherein the graphical user interface represents a computerized game.

6. The data processing system of claim 1, wherein a feature of the feature vector represents a performance measurement for a computer game that requests input and measures received input.

7. The data processing system of claim 6, wherein the performance measurement for the computer game comprises one of a click rate measurement, a click delay measurement, a click accuracy measurement, an overall score measurement, and a miss rate measurement.

8. The data processing system of claim 1, wherein a feature of the feature vector represents a demographic of a user of the client device.

9. The data processing system of claim 1, wherein the one or more measurements of eye movements comprise one or more of: a mean of values representing eye fixation durations, a number of measured eye fixations, a mean of saccadic movement, number of saccadic movements, sum of saccadic movements, a sum of values representing eye fixations, a number of gaze visits to a specified area on the graphical user interface, and a mean time of values representing gaze visits.

10. The data processing system of claim 1, wherein a feature of the feature vector represents one of: a designation of a font of displayed text, and a font rating.

11. The data processing system of claim 1, wherein the machine learning logic comprises neural network logic.

12. The data processing system of claim 1, further comprising a feature transform logic engine that is configured to normalize each feature of the features of the feature vector for use by the machine learning logic.

13. The data processing system of claim 1, wherein a feature of the feature vector represents a performance measure for mouse-tracking movements.

14. The data processing system of claim 13, wherein the performance measure mouse-tracking comprises one of: mean of mouse fixation, number of mouse fixations, sum of mouse fixations, mean of saccadic movement, number of saccadic movements, sum of saccadic movements, and a number of mouse visits to an area of interest.

15. The data processing system of claim 1, the operations further comprising updating a font for the user interface of the client device responsive to determining the prediction value.

16. A method for processing, by at least one processor in communication with a memory, a feature vector that comprises features representing one or more features that are indicative of dyslexic behavior, the method comprising:
receiving, at the at least one processor from a camera, data representing measurements of eye movements of a user of a client device as the user reads text rendered on a graphical user interface of the client device;
receiving, at the at least one processor from the graphical user interface of the client device, data representing one or more interactions with the graphical user interface of the client device;
generating, by the at least one processor based on the data representing one or more interactions with the graphical user interface of the client device and the data representing the measurements of the eye movements, the feature vector, wherein a feature of the feature vector represents one or more measurements of the eye movements of the user of the client device or other data indicative of dyslexic behavior;
determining, by the at least one processor using machine learning logic, a classification metric for each feature of the feature vector, the machine learning logic being trained by operations comprising:
  selecting a set of features representing performance measurements for a set of users interacting with user interfaces;
  receiving, for the set of users, label data specifying whether the user is dyslexic;
  training the machine learning logic using the set of features and the label data; and iteratively removing one or more features from the set of features until an accuracy of the machine learning logic satisfies a threshold accuracy to generate a final set of features for including the feature vector; and generating, by the at least one processor, a prediction value indicative of a predicted likelihood of dyslexia for the user by performing operations comprising:

assigning to each feature of the feature vector, based on the classification metric of the respective feature, a prediction weight;

determining the prediction value based on that prediction weight for each feature of the feature vector; and outputting, for rendering on a display, a representation of the prediction value.

17. The method of claim 16, further comprising:

generating data for the graphical user interface, the graphical user interface, when rendered on the client device, displaying:

a first visual representation of one or more letters of text that represent a selectable control configured to be activated in response to a visual or auditory prompt; and a second visual representation of one or more letters of text that represent another selectable control configured to be activated in response to a visual or an auditory prompt, wherein the first visual representation is juxtaposed to the second visual representation in the graphical user interface.

18. The method of claim 17, further comprising:

storing, by a data repository, data representing visual representations of each of a library of selectable controls that comprise text and data representing auditory prompts that correspond to the first and second visual representations;

determining a cognitive skill that is being evaluated; and selecting from the data repository, data representing the first visual representation and data representing the second visual representation based on the determination of the cognitive skill that is being evaluated.

19. The method of claim 16, wherein the graphical user interface represents a computerized game.

20. The method of claim 16, further comprising:

recording a performance measurement for a computer game by requesting input and measuring received input.

* * * * *